US009498271B2

(12) United States Patent
Osborne et al.

(10) Patent No.: US 9,498,271 B2
(45) Date of Patent: Nov. 22, 2016

(54) COAXIAL NEEDLE CANNULA WITH DISTAL SPIRAL MIXER AND SIDE PORTS FOR FLUID INJECTION

(75) Inventors: Thomas A. Osborne, Bloomington, IN (US); Jeffry S. Melsheimer, Springville, IN (US); Christopher D. Bosel, Bloomington, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 257 days.

(21) Appl. No.: 12/914,167

(22) Filed: Oct. 28, 2010

(65) Prior Publication Data

US 2011/0106054 A1 May 5, 2011

Related U.S. Application Data

(60) Provisional application No. 61/255,886, filed on Oct. 29, 2009.

(51) Int. Cl.
| | |
|---|---|
| *A61B 17/88* | (2006.01) |
| *A61M 5/315* | (2006.01) |
| *B01F 5/06* | (2006.01) |
| *A61M 5/19* | (2006.01) |

(52) U.S. Cl.
CPC ....... *A61B 17/8816* (2013.01); *A61B 17/8822* (2013.01); *B01F 5/0615* (2013.01); *A61B 2017/8838* (2013.01); *A61M 5/19* (2013.01); *A61M 5/31581* (2013.01)

(58) Field of Classification Search
CPC .. A61M 25/09; A61M 25/00; A61M 25/003; A61M 1/0068; A61M 5/19
USPC .......... 604/19, 22–24, 39, 82–93, 191, 213, 604/290, 500, 506, 518–520, 41–42; 606/213; 366/336–337
See application file for complete search history.

(56) References Cited

U.S. PATENT DOCUMENTS

| | | | |
|---|---|---|---|
| 203,387 A | 5/1878 | Stohlmann et al. | |
| 319,698 A | 6/1885 | Graefe | |
| 3,815,878 A * | 6/1974 | Baskas et al. | 206/222 |
| 4,631,055 A * | 12/1986 | Redl et al. | 604/82 |
| 4,796,622 A | 1/1989 | Lu et al. | |
| 4,808,184 A * | 2/1989 | Tepic | 604/518 |
| 4,979,518 A | 12/1990 | Itoh et al. | |
| 6,033,401 A * | 3/2000 | Edwards et al. | 606/41 |
| 6,053,899 A * | 4/2000 | Slanda et al. | 604/500 |
| 6,190,380 B1 | 2/2001 | Abela | |
| 6,224,591 B1 | 5/2001 | Claren et al. | |
| 6,379,378 B1 | 4/2002 | Werneth et al. | |

(Continued)

FOREIGN PATENT DOCUMENTS

| | | |
|---|---|---|
| WO | WO 83/03961 | 11/1983 |
| WO | WO 01/68160 | 9/2001 |
| WO | WO 2008/106357 | 9/2008 |

*Primary Examiner* — Kami A Bosworth
*Assistant Examiner* — Matthew A Engel
(74) *Attorney, Agent, or Firm* — Woodard, Emhardt, Moriarty, McNett & Henry LLP

(57) ABSTRACT

Disclosed is a multi-lumen mixing device that includes a first and second lumen constructed and arranged to separately pass a first and second reagent to a mixing chamber in the device, where the mixing chamber includes a mixing feature that mixes the first and second reagents. The disclosed multi-lumen mixing device may also include a port in fluid communication with the reaction mixing to permit the product of the combined reagents to be injected into a patent.

21 Claims, 7 Drawing Sheets

(56) References Cited

U.S. PATENT DOCUMENTS

| | | |
|---|---|---|
| 6,454,739 B1* | 9/2002 | Chang .............................. 604/82 |
| 6,576,001 B2 | 6/2003 | Werneth et al. |
| 6,648,852 B2* | 11/2003 | Wirt et al. ...................... 604/86 |
| 6,796,966 B2* | 9/2004 | Thomas ........................ 604/191 |
| 6,824,555 B1 | 11/2004 | Towler et al. |
| 6,832,995 B1 | 12/2004 | Towler et al. |
| 6,905,510 B2 | 6/2005 | Saab |
| 7,097,642 B1 | 8/2006 | Sprague et al. |
| 7,118,591 B2 | 10/2006 | Frank et al. |
| 7,211,066 B1 | 5/2007 | Merrill |
| 7,485,107 B2 | 2/2009 | DiFiore et al. |
| 7,490,738 B2 | 2/2009 | Crews |
| 7,572,257 B2 | 8/2009 | Whayne et al. |
| 7,575,131 B2* | 8/2009 | Feinberg et al. ............. 222/137 |
| 7,811,291 B2* | 10/2010 | Liu et al. ........................ 606/94 |
| 2002/0016621 A1 | 2/2002 | Werneth et al. |
| 2002/0049409 A1 | 4/2002 | Noda et al. |
| 2002/0049484 A1 | 4/2002 | Werneth et al. |
| 2004/0005295 A1 | 1/2004 | Lee et al. |
| 2005/0085769 A1 | 4/2005 | MacMahon et al. |
| 2005/0187542 A1 | 8/2005 | Auge, II et al. |
| 2006/0253088 A1 | 11/2006 | Chow et al. |
| 2007/0027449 A1 | 2/2007 | Godara et al. |
| 2007/0167776 A1 | 7/2007 | Kochavi et al. |
| 2007/0173786 A1 | 7/2007 | Recinella et al. |
| 2007/0203479 A1 | 8/2007 | Auth et al. |
| 2008/0103564 A1 | 5/2008 | Burkinshaw et al. |
| 2008/0243112 A1 | 10/2008 | De Neve |
| 2010/0145304 A1* | 6/2010 | Cressman ............. A61B 18/06 604/506 |
| 2010/0268158 A1* | 10/2010 | Porter ............................ 604/82 |

* cited by examiner

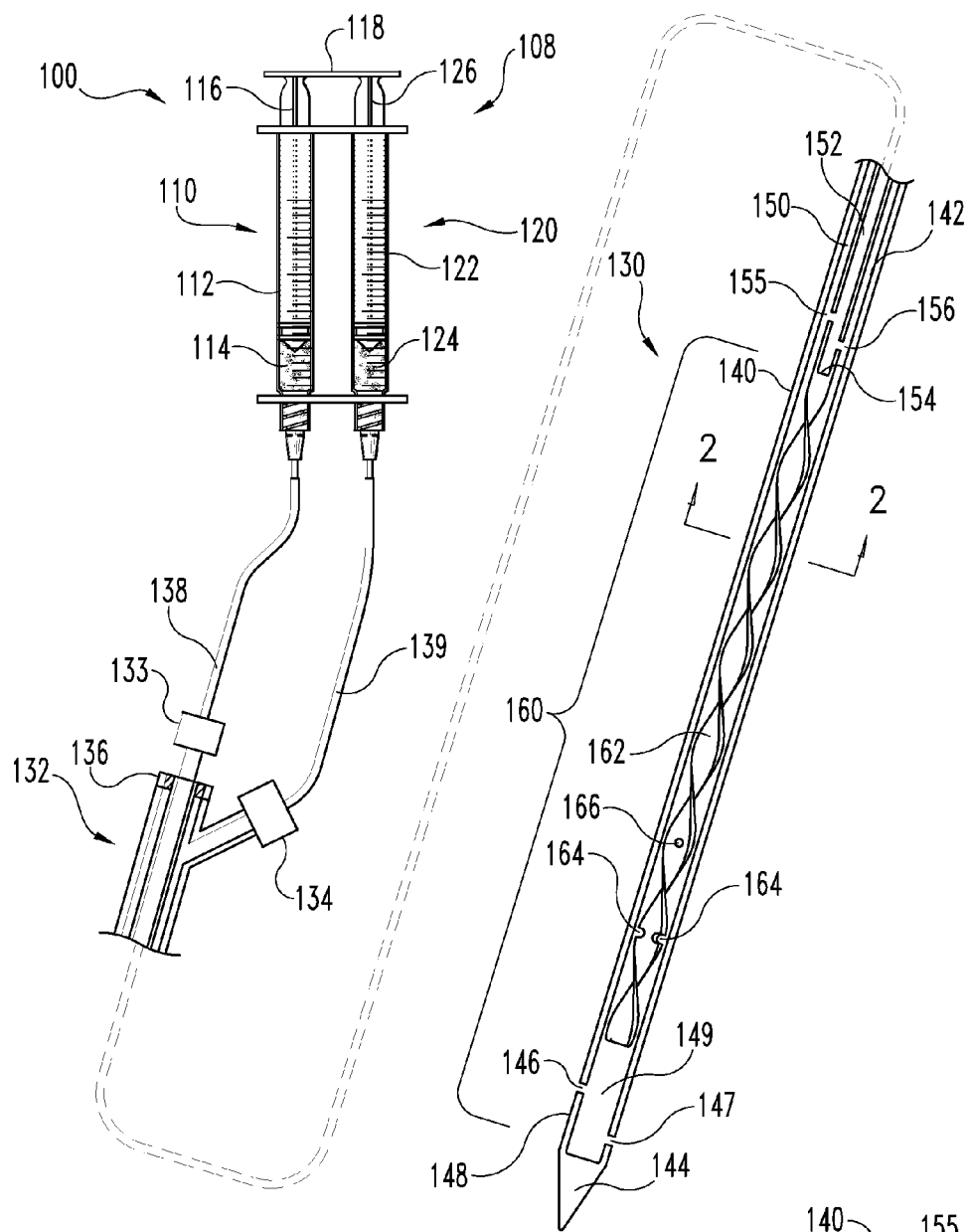
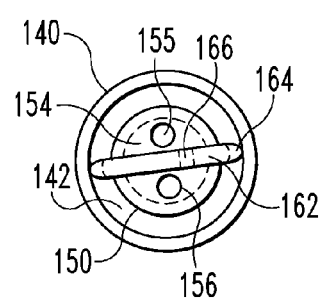
Fig. 1
Fig. 2

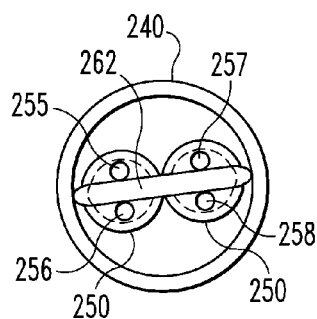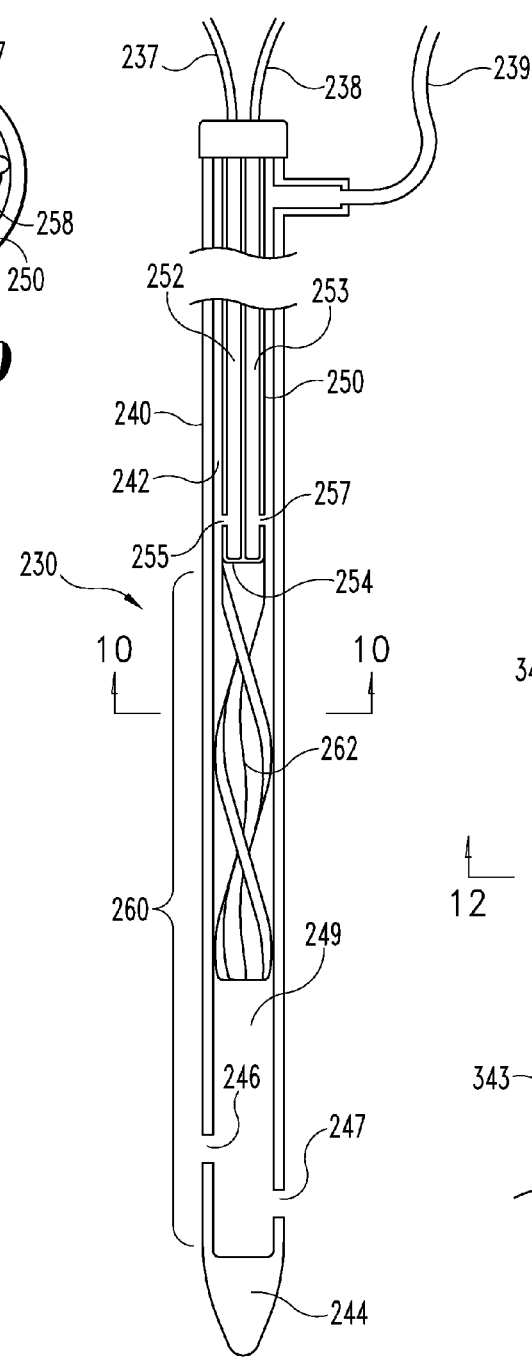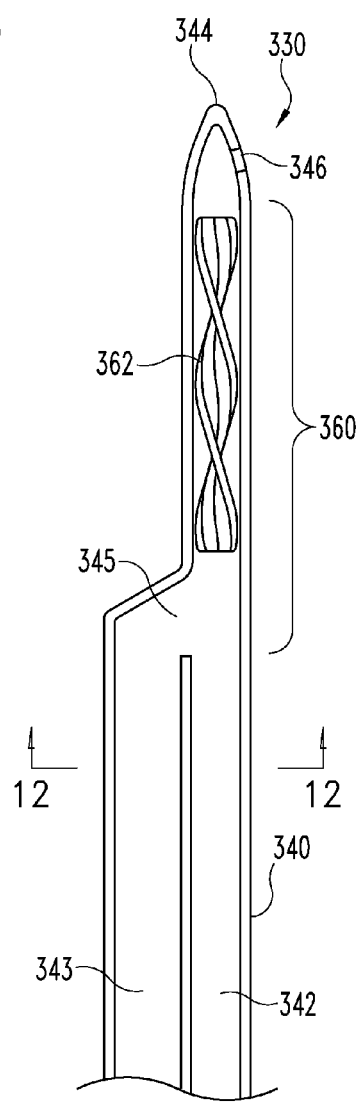
Fig. 10
Fig. 12
Fig. 9
Fig. 11

COAXIAL NEEDLE CANNULA WITH DISTAL SPIRAL MIXER AND SIDE PORTS FOR FLUID INJECTION

REFERENCE TO RELATED APPLICATIONS

The present application claims the benefit of U.S. Provisional Patent Application Ser. No. 61/255,886 filed Oct. 29, 2009 entitled MULTI-LUMEN MEDICAL MIXING DEVICE which is hereby incorporated by reference in its entirety.

BACKGROUND

The present disclosure concerns medical devices that serve to mix two or more components. In particular, it concerns medical devices in which components are passed through separate lumens and then mixed during a procedure for treating a patient.

As further background, there are a variety of medical applications in which two or more flowable components are mixed together for treatment of the patient. As examples, tissue ablation systems have been suggested in which chemicals which react exothermally with each other are mixed and injected into the patient to destroy undesired tissue such as cancerous or precancerous tissue. As additional examples, systems for injection of bone cements have also been suggested wherein two components are mixed just prior to introduction into the patient, whereupon the mixture hardens.

Needs exist for improved or alternative medical devices for achieving admixture of two or more flowable components as a part of a patient treatment regimen. In certain aspects, the present disclosure is addressed to these needs.

SUMMARY

In certain aspects, the present disclosure relates to multi-lumen medical devices that include first and second lumens for passage of first and second reagent materials, respectively. The devices also include a mixing chamber in fluid communication with the first and second lumens, and a mixing element in the chamber that mixes the first and second reagent materials during flow.

Additional aspects of the disclosure as well as features and advantages thereof will be apparent from the further descriptions herein.

BRIEF DESCRIPTION OF THE FIGURES

FIG. 1 is a perspective view of a multiple reagent injection system including a partial sectional view of a multi-lumen mixing device.

FIG. 2 is an in sectional view of the multi-lumen mixing device of FIG. 1 along lines 2-2.

FIG. 9 is a cross sectional elevational view of an alternative embodiment of a multi-lumen mixing device.

FIG. 10 is a cross sectional view of the FIG. 9 multi-lumen mixing device taken along section line 10-10.

FIG. 11 is a partial cross sectional view of an alternative embodiment of a multi-lumen mixing device.

FIG. 12 is a cross sectional view of the FIG. 11 multi-lumen mixing device taken along section line 12-12.

DETAILED DESCRIPTION

Figure 3:
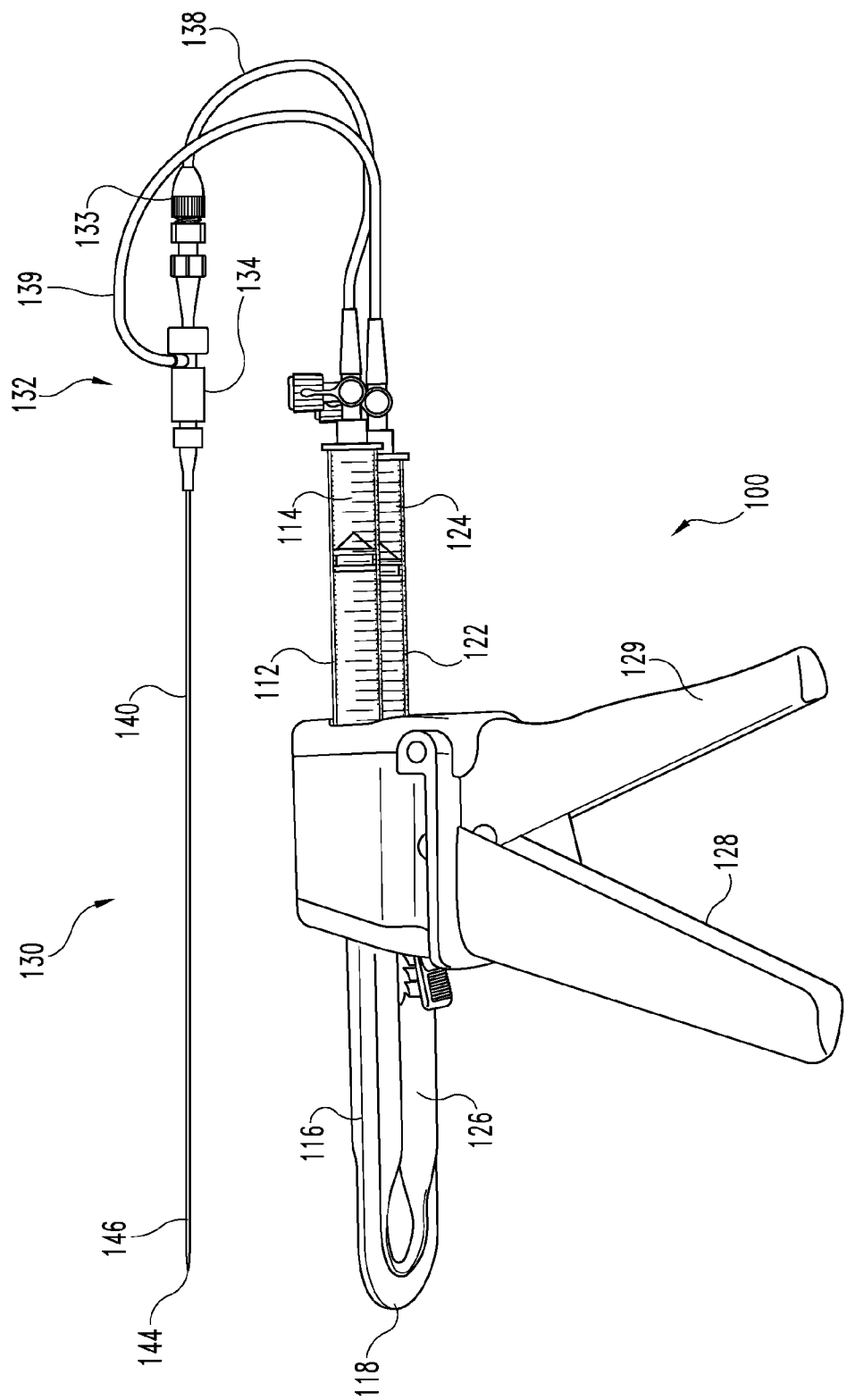
FIG. 3 is a perspective view of an embodiment of the FIG. 1 multiple reagent injection system including a multi-lumen mixing device.

Reference will now be made to certain embodiments and specific language will be used to describe the same. It will nevertheless be understood that no limitation of the scope of this disclosure and the claims is thereby intended, such alterations, further modifications and further applications of the principles described herein being contemplated as would normally occur to one skilled in the art to which this disclosure relates. In several figures, where there are the same or similar elements, those elements are designated with the same or similar reference numerals.

Referring now to FIGS. 1 and 2, multiple reagent injection system 100 is illustrated including infusion system 108 and multi-lumen mixing device 130. Infusion system 108 generally includes infusion devices 110 and 120, including reservoirs 112 and 122 containing reagents 114 and 124 and actuators 116 and 126. Actuators 116 and 126 are linked together by coupling 118. Multiple reagent injection system 100 is used to mix and inject reagents 114 and 124 into a human patient. Several non-limiting examples of embodiments of multiple reagent injection system 100 in use to treat specific conditions are disclosed herein.

Multi-lumen mixing device 130 generally includes an elongate element 140, for example a needle or catheter, defining lumen 142 and cannula 150 defining lumen 152. The proximal end of multi-lumen mixing device 130 includes hub 132 generally including coupling 134, cannula support 136 and coupling 133. Coupling 134 provides access to lumen 142. Cannula support 136 supports and secures cannula 150 within elongate element 140 in a coaxial arrangement. Coupling 133 provides access to lumen 152. Tube 138 couples reservoir 112 to lumen 152 through coupling 133 while tube 139 couples reservoir 122 to lumen 142 through coupling 134.

The distal portion of multi-lumen mixing device 130 defines reaction or mixing chamber 160 which generally includes mixing feature 162, reservoir 149 and ports 146 and 147. In the illustrated embodiment, mixing feature 162 is a spiral mixer that optionally includes notches 164 and/or aperture(s) 166. In certain embodiments, such spiral mixer can be formed as a generally planar structure that has a twisted pattern in its longitudinal axis providing a longitudinal spiral. Such structures can be formed from flat planar lengths of material that have been subjected to twisting forces or can be machined, molded or otherwise manufactured to originally have a spiral shape. Other embodiments can use mixing feature(s) with other mixer configurations, including, but not limited to, a flow dividing static mixer, an alternating spiral mixer, and a static mixer with overlapping semi-helical baffles. Mixing feature 162 can be attached to or integrally formed with cannula 150 and/or catheter 140 or mixing feature 162 can float in reaction chamber 160. In certain embodiments in which mixing feature 162 is integrally formed with cannula 150, an original length of cannulated material can be flattened to a generally planar condition along an end segment thereof. The flattening can block or close the lumen(s) of the cannulated material, either alone or potentially in combination with a substance introduced into the lumen(s) of all or part of the segment which has been, or is to be, flattened. Suitable substances of these purposes can include adhesives, glues, polymerizable material, solders or other bonding agents. Thermal or other welding or fusion of the opposed walls of the flattened segment can also be used to facilitate closure of the lumen(s) of the flattened segment and/or to assist in imparting a permanent predictable shape to the spiral mixer. In instances in which the mixing feature 162, is integrally formed with cannula 150, an outer wall of cannula 150 that is integral with the outer wall of mixing feature 162 can be provided.

Mixing feature 162 can be configured to be rotationally constrained with respect to elongate element 140 or mixing feature 162 can be configured to rotate with respect to elongate element 140. In embodiments where mixing feature 162 can rotate with respect to elongate element 140, such rotation can be driven by the flow of reagents 114 and 124 and/or mixing feature 162 can be coupled to an external power source, for example, by rotating cannula 150 (e.g., an embodiment of FIG. 4 described below).

At the distal end of multi-lumen mixing device 130 is tip 144. Reservoir 149 is defined by the lumen between the distal end of mixing feature 162 and tip 144. Ports 146 and 147 provide access from reaction chamber 160 to the area outside of multi-lumen mixing device 130 in the patient being treated. Ports 155 and 156 provide access between lumen 152 and lumen 142 and is the location where reagents 114 and 124 first communicate before passing through mixing feature 162. The distal end of lumen 152 is blocked by occlusion 154 thereby forcing reagent 114 to intermix with reagent 124.

Infusion system 108 provides for simultaneous delivery of reagents 114 and 124 to the patient from reservoirs 112 and 122 through movement of coupling 118 and thereby actuators 116 and 126. As reagents 114 and 124 are expelled from reservoirs 112 and 122, reagent 114 passes through tube 138 to lumen 152 while reagent 124 passes through tube 139 to lumen 142. Reagent 114 then is expelled from lumen 152 through ports 155 and/or 156 to co-mingle with reagent 124 in lumen 142. As reagents 114 and 124 proceed distally down multi-lumen mixing device 130 through continued movement of actuators 116 and 126, reagents 114 and 124 enter reaction chamber 160 where mixing feature 162 produces patterns of blending and/or radial mixing to mix reagents 114 and 124 together. In some embodiments, mixing feature 162 may also promote chemical reaction between reagents 114 and 124. After passing through mixing feature 162 mixed reagents 114 and 124 may optionally enter reservoir 149 that provides an optional delay period before the mixed reagents 114 and 124 are expelled from multi-lumen mixing device 130 through ports 146 and 147. The relative length and diameter of reservoir 149 can be selected to provide for a delay period by permitting reagent 114 and 124 to chemically react together before being expelled from multi-lumen mixing device 130. In some embodiments, reservoir 149 may also provide thermal energy storage in the distal portion of multi-lumen mixing device 130. Reservoir 149 can be optionally omitted by positioning the distal end of mixing feature 162 at or near tip 144 and/or ports 146 and 147.

Tip 144 of multi-lumen mixing device 130 can be configured in several different ways. One embodiment, tip 144 includes a cutting and/or burrowing feature on the distal most end permitting elongate element 140 to be inserted directly into tissue such as skin, organs, arteries, veins and bone. For example, tip 144 may include a beveled cutting edge, a saw-toothed cutting edge, a pointed end, a trocar tip, or any other configuration desired for cutting and/or burrowing into tissue. In other embodiments, tip 144 may be blunted, permitting elongate element 140 to be inserted into an arterial or venous structure and to be advanced therethrough to tissue targeted for treatment. Such an embodiment generally requires a separate introducer as is known in the art for laparoscopic procedures and for venous or arterial access.

In this regard, in various embodiments, elongate element 140, cannula 150 and mixing feature 162 can be constructed of either rigid or flexible materials. In embodiments in which elongate element 140 is configured as a needle with a cutting/burrowing feature on tip 144 to provide direct access to bodily tissue, then elongate element 140 can be made of a rigid material such as a metal or a relatively rigid polymer. In other embodiments where multi-lumen mixing device 130 is configured as a catheter to be introduced through arterial or venous access or into a body cavity through a laparoscopic method, then elongate element 140, mixing feature 162 and cannula 150 may be constructed of a flexible material such as a relatively flexible polymer or flexible metal material. In other embodiments, multi-lumen mixing device 130 includes a cutting/burrowing feature on tip 144 while being constructed of a flexible material. In yet other embodiments, multi-lumen mixing device 130 includes a blunt tip 144 while being constructed of a rigid material. As examples, elongate element 140, cannula 150 and mixing feature 162 can be constructed from metals such as stainless steel (SS) material including, but not limited to 302, 304 or 316 series SS, nitinol (a superelastic nickel-titanium alloy), nickel, cobalt chromium or MP35N, and/or from polymeric materials such as silicone, polyethylene terephthalate, polyurethane, polyamide (e.g. a Nylon), polyester, polyorthoester, polyanhydride, polyether sulfone, polycarbonate, polypropylene, polyethylene (including high molecular weight polyethylene), polytetrafluoroethylene, or polyetheretherketone (PEEK).

In one embodiment, a user may apply a force to coupling 118 to contemporaneously move actuators 116 and 126 to simultaneously deliver reagents 114 and 124 to multi-lumen mixing device 130 through tubes 138 and 139. In other embodiments, a user may selectively activate a computer controlled mechanism that acts upon coupling 118 to move actuators 116 and 126 and yet in other embodiments, reservoirs 112 and 122 may not be physically coupled to one another and actuators 116 and 126 may be separately adjusted to dispense reagents 114 and 124 simultaneously or in selected sequence. For example, individual infusion pumps could replace linked infusion devices 110 and 120 and in yet another embodiment, actuators 116 and 126 could be pulsed relative to one another to provide a different mixing dynamic within multi-lumen mixing device 130.

Multi-lumen mixing device 130 may optionally include visualization marker 148 near tip 144 and/or ports 146 and 147 to provide enhanced visualization during insertion and use. For example, when utilizing ultrasonic visualization techniques, visualization marker 148 could comprise an echogenic marker such as a series of small dimple-like indentations on the outer surface of elongate element 140, for example those used on ECHOTIP® Echogenic Needles available from Cook Medical, Bloomington, Ind., USA, to provide enhanced ultrasonic return. In other embodiments, a radiopaque marker could be used to provide enhanced x-ray response during fluoroscopy or other x-ray visualization techniques. Visualization marker 148 may improve the ability of an interventionalist to monitor the position of tip 144 and/or ports 146 and 147 within a patient's body during use.

Referring now to FIG. 3, an embodiment of system 100 is illustrated including reservoirs 112 and 122 containing reagents 114 and 124, actuators 116 and 126 coupled by coupling 118. Actuators 116 and 126 and reservoirs 112 and 122 are held in injector 128 that is capable of simultaneously moving actuators 116 and 126 by actuating trigger grip 129. Reservoirs 112 and 122 are coupled through tubing 138 and 139 to multi-lumen mixing device 130 through couplings 134 and 133. In the illustrated embodiment, multi-lumen mixing device 130 is comparatively rigid with a needle like catheter 140 including a pencil tip 144 and side port 146.

Figure 4:
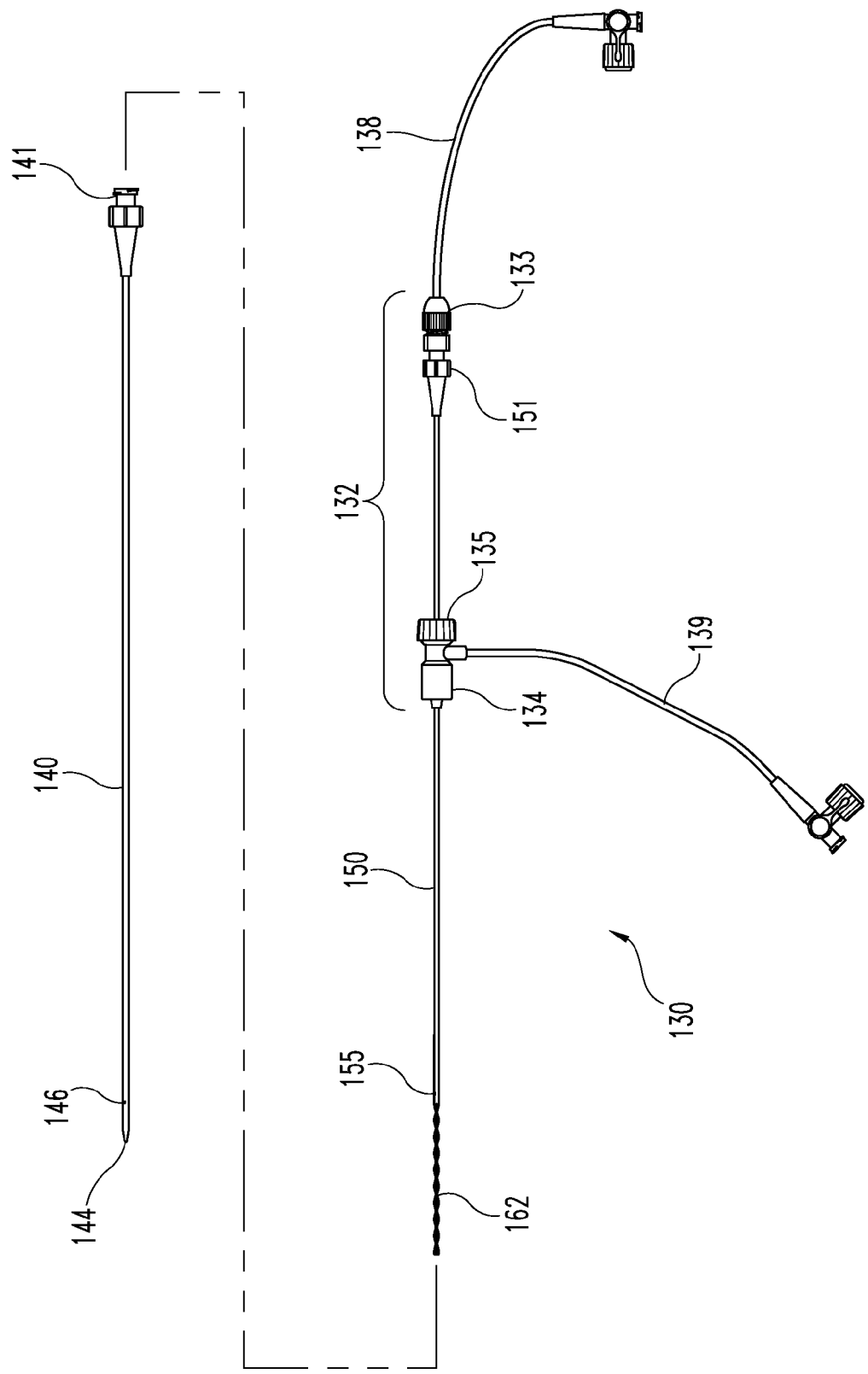
FIG. 4 is an exploded view of the multiple lumen mixing device of FIG. 3.
Figure 5:
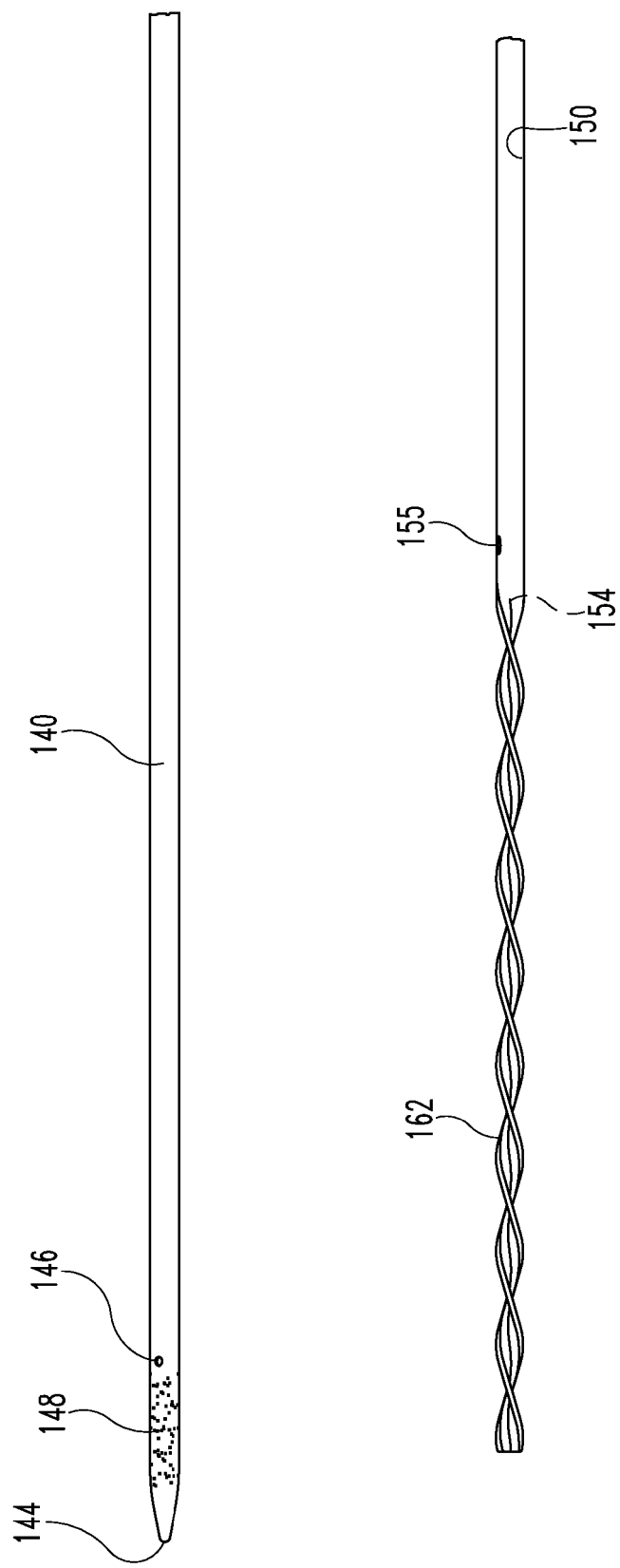
FIG. 5 is a partial view of the distal portion of multi-lumen mixing device of FIG. 4.

Referring now to FIGS. 4 and 5, the multi-lumen mixing device 130 from FIG. 3 is separately illustrated as elongate element 140 and cannula 150. Elongate element 140 includes, luer fitting 141, tip 144, port 146 and visualization marker 148. In the specific illustrated embodiment, element 140 is a metallic needle and tip 144 is a pencil point. Cannula 150 is formed from a metallic tube in the illustrated embodiment with coupling 133 including a proximal luer fitting with the distal portion of metallic tube 150 forming mixing portion 162 by being crimped and formed into a spiral mixer configuration with port 155 positioned proximal from the crimping point. In this embodiment, the crimp in the metallic tube forms occlusion 154. In one embodiment, as illustrated in FIG. 2, ports 155 and 156 are positioned on opposite sides of the crimped metallic tube defining mixing feature 162. Cannula 150 passes through septum 135 on coupling 134. Coupling 134 is constructed and arranged to permit luer fitting 141 on catheter 140 to seal therewith so that cannula 150 passes through the lumen of catheter 140. Coupling 133 attaches to luer fitting 151 on the proximal end of cannula 150. In an alternative embodiment, coupling 133 permits relative rotation between cannula 150 and tube 138 permitting cannula 150 to be rotated with respect to element 140, thereby rotating mixing feature 162 inside element 140.

Figure 6:
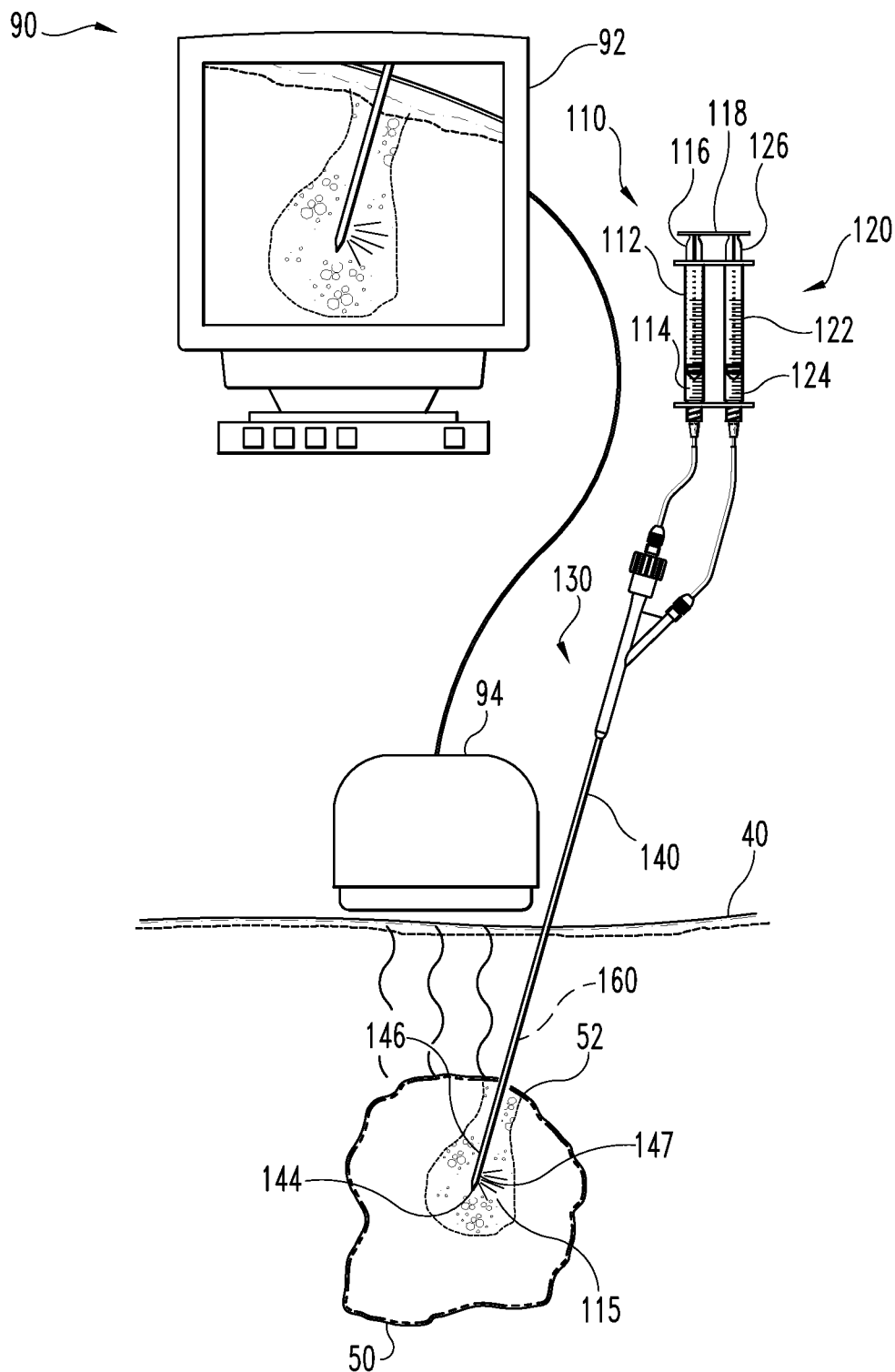
FIG. 6 illustrates a multiple reagent injection system configured as a thermal chemical ablation system including an ultrasonic imaging system.

Referring now to FIG. 6, an embodiment of multiple reagent injection system 100 is illustrated as constructed and arranged for use as a thermochemical ablation device. In general, the illustrated thermochemical ablation device infuses thermochemical ablation reagents that exothermically react when combined. FIG. 6 generally illustrates multi-lumen mixing device 130 inserted into target tissue 50 (e.g., a tumor) under skin 40 of a patient. Ports 146 and 147 are in fluid communication with reservoirs 112 and 122 and ablation reagents 114 and 124 with reaction chamber 160 there between so that combined reagent 115 injects when coupling 118 (and actuators 116 and 126) is moved thereby ablating tissue 52 from target tissue 50. In this embodiment, reagents 114 and 124 are selected to react and generate an exothermic chemical reaction. Such reagents can, for example, be any of those identified herein. Utilized in this way, multiple reagent injection system 100 provides for simultaneous infusion of reagents 114 and 124 as combined reagent 115 into targeted tissue 50 with an exothermic chemical reaction from combined reagent 115 ablating targeted tissue 50. In the illustrated embodiment, reagents 114 and 124 are infused in equal proportions.

In other embodiments where reagents 114 and 124 are infused in different proportions, reservoir 112 may have a different configuration (e.g., different cross-sectional area) than reservoir 122 so that different amounts of fluid are dispensed from reservoir 112 and 122 when actuators 116 and 126 are simultaneously moved (e.g., using coupler 118).

The heat generated from the chemical reaction of combined reagent 115 is sufficient to ablate at least a portion of target tissue 50 surrounding tip 144. Thermochemical ablation reagents 114 and 124 infused into the target tissue 50 can be selected to provide a suitable energy disposition to target tissue 50 and to optionally provide other features such as hyperosmolarity. In some embodiments, reagent 114 may comprise an acid. For example, an acid selected from the group consisting of an acetic acid, peracetic acid, hydrochloric acid, hydrobromic acid, hydriodic acid, sulfuric acid, nitric acid, nitrous acid, perchloric acid, phosphoric acid, oxalic acid, pyruvic acid, malonic acid, amino acids (e.g., carboxylic acid derivatives), and the like. Similarly, reagent 124 may comprise a base. For example, a base selected from the group consisting of KOH, NaOH, $NH_4OH$, $Ca(OH)_2$, $NaHCO_3$, $K_2CO_3$, BuLi, NaOEt or NaSEt (e.g., Na or K salts of alkoxides or their analogues), NaH, KH, particular amines, and the like.

In some embodiments, the concentration of the base reagent or the acid reagent can be selected so as to fully neutralize the acid and base load applied to the targeted tissue 50 after the thermochemical ablation reaction (e.g. resulting in a mixture having a pH in the range of about 6 to about 8, desirably about 7). In other embodiments, the concentration of the base reagent or the acid reagent can be selected so as to partially neutralize the acid or base load while generating heat energy, thereby providing heated solution with a limited and safe level of remaining acid or base load.

In various embodiments, the particular acid and the particular base may be selected to provide a desired heat generation and low toxicity byproduct. For example, in one embodiment, reagent 114 may be either acetic acid or hydrochloric acid, while reagent 124 may be NaOH, NaOEt or $NH_4OH$. Multiple reagent injection system 100 maintains reagent 114 separate from reagent 124 until reagents 114 and 124 reach reaction chamber 160 and are subsequently infused as combined reagents 115 into target tissue 50 allowing reagents 114 and 124 to chemically react to generate ablation heat energy. Such chemical reaction can begin within the distal portion of multi-lumen mixing device 130 in reaction chamber 160 thereby heating the distal portion of element 140 that may also aid the ablation of target tissue 50. In some embodiments, the byproducts from the chemical reaction of reagents 114 and 124 may further benefit the ablation process, for example, due to hyperosmolarity of combined reagents 115 to target tissue 50.

In yet other embodiments, reagents 114 and 124 may include other reactive substances. For example, reagent 114 may comprise electrophiles, and reagent 124 may comprise nucleophiles. In yet another embodiment, reagent 114 may include electrophiles from the group consisting of acetic anhydride, acetyl chloride, acetyl bromide, other anhydrides, other acid halides and the like while reagent 124 may comprise a nucleophile selected from the group consisting of alkoxides, thio analogues, mercaptans (e.g., sulfhydryl), some amines and the like. Other nucleophiles could include alcohols, sugar molecules, water, and endogenous nucleophiles. In other embodiments, reagent 124 may comprise a nucleophile selected from the group of previously described bases (e.g., NaOH, NaOEt or $NH_4OH$ or the like). Thus, some embodiments of multiple reagent injection system 100 can infuse an electrophile (such as acetyl chloride) with a nucleophile (such as NaOH) that chemically react with one another. The byproducts of the chemical reaction provide therapeutically significant heat generation while at least partially neutralizing any acid (or base) load.

In other embodiments, reagents 114 and 124 may include other reactive substances. For example, reagent 114 may comprise a particular oxidizing agent, and reagent 124 may comprise a certain reducing agent. In yet other embodiments, the thermochemical ablation reagents could be selected to have useful imaging or other analyzable features (e.g., fluorescence, nuclear isotopes, MR imaging characteristics, or the like) to permit the evaluation of reagent distribution in target tissue 50 and throughout the body before and after treatment.

In some embodiments, one or both of reagents 114 and/or 124 can be mixed with a denaturing agent that enhances the tissue ablation process. For example, a denaturing agent such as a sclerosant, detergent, urea or sodium perchlorite (or another substance from the Hofmeister series) can be mixed with the reagent 114 or reagent 124 prior to injection through multi-lumen mixing device 130. The denaturing agent may react upon targeted tissue 50 to enhance the ablation effect caused by thermochemical reaction of reagents 114 and 124.

In yet other embodiments, a drug may be added to one or both of the thermochemical reagents 114 and 124 to provide a pharmacological effect on target tissue 50 in addition to any thermochemical ablation effects. For example, a chemotherapy drug can be added to reagent 114 and/or 124 prior to injection through multi-lumen device 130. The chemotherapy drug can then be administered to the target tissue 50 through multi-lumen mixing device 130 to provide the pharmacological effect contemporaneously with the ablation effect from thermochemical reaction from combined reagent 115. In yet another embodiment, multi-lumen mixing device 130 can be modified with an additional lumen that bypasses reaction chamber 160 and provides for simultaneous injection of a drug at or near tip 144, or near ports 146 and 147. In another embodiment, such an additional lumen could allow simultaneous injection into reaction chamber 160 (such as the configuration illustrated in FIGS. 9-10, discussed below).

Still referring to FIG. 6, some embodiments of multiple reagent injection system 100 may include the use of medical imaging system 90 to provide real-time monitoring of multi-lumen mixing device 130 during its insertion and delivery of reagents 114 and 124 as combined reagents 115. For example, as illustrated in FIG. 6, medical imaging system 90 could include an ultrasonic imaging device to enable a user to view the distal portion of multi-lumen mixing device 130 in target tissue 50. Imaging system 90 may include probe 94 such as the illustrated ultrasonic probe. Probe 94 can be manipulated on the outside of a patient's body or within a body cavity to provide imaging of target tissue 50 and/or multi-lumen mixing device 130. Probe 94 may be connected to a display system 92 that interprets the signal from probe 94 and generates a display of the targeted portion of the patient's body. For example, as illustrated in FIG. 6, display system 92 shows distal portion of multi-lumen mixing device 130 as inserted into target tissue 50 for delivery of combined reagent 115. In other embodiments, imaging systems may comprise other types of imaging systems other than ultrasound imaging. For example, imaging system 90 could include a fluoroscope, a CT imaging system or the like. In some embodiments, the outside of catheter 140 may include depth markers that are directly viewable by a user to determine the depth of insertion through skin 40 to indicate the approximate depth of insertion. In addition, such depth markers can be spaced at regular intervals (such as centimeters) for use as a scale to measure the relative size of internal structures (such as tumors, etc.).

Figure 7:
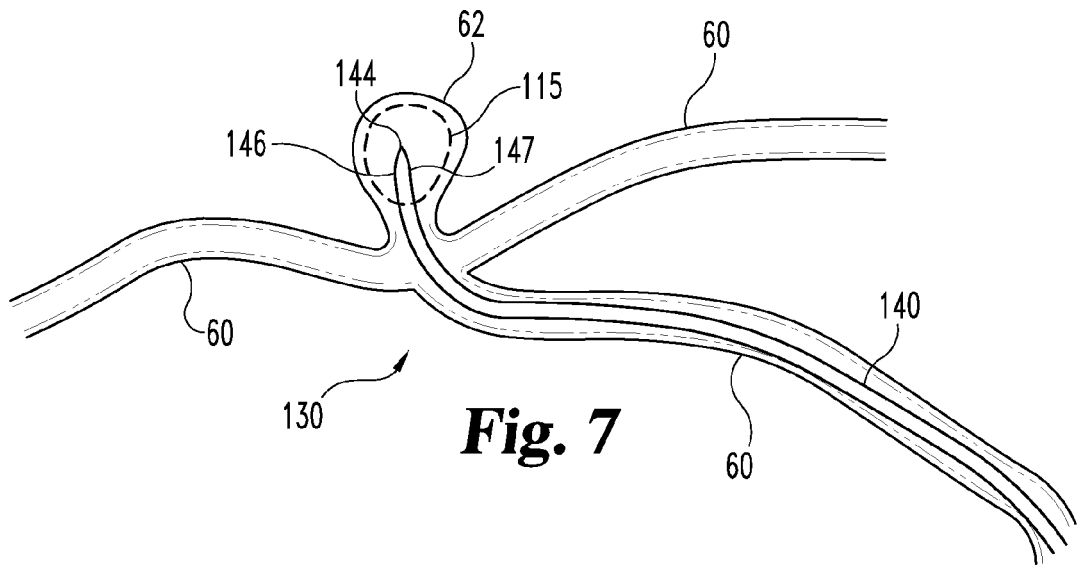
FIG. 7 is a partial cross sectional view of a flexible multi-lumen mixing device filling an arterial aneurism.

Referring now to FIG. 7, an embodiment of a comparatively flexible multi-lumen mixing device 130 is illustrated as constructed and arranged for treating an aneurism in an arterial wall. Illustrated are arteries 60 containing aneurism 62 with element 140 advanced through artery 60 with tip 144 and ports 146 and 147 positioned within aneurism 62. Multi-lumen mixing device 130 has injected combined reagents 115 into aneurism 62. In this embodiment, combined reagents 115 polymerize and/or promote a thrombolytic reaction within aneurism 62 to seal off aneurism 62. As discussed elsewhere, a medical imaging device can be used to assist in the insertion of multi-lumen mixing device 130 into aneurism 62 and the subsequent injection of combined reagent 115 to substantially fill aneurism 62 with the resultant polymer and/or clot. In an alternative embodiment, combined reagent 115 forms a biocompatible polymer that substantially fills aneurism 62.

Figure 8A:
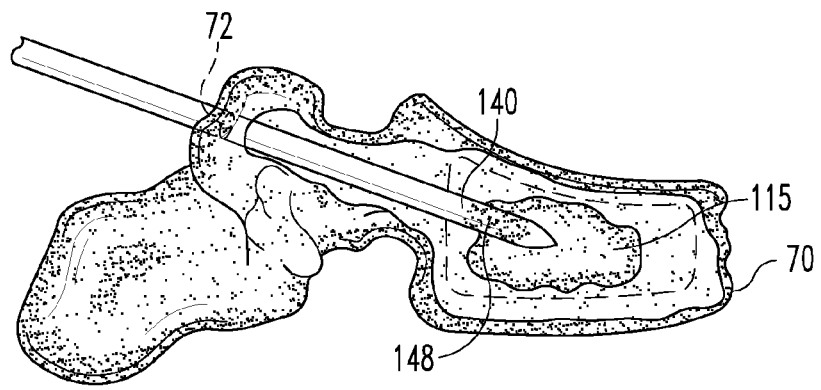
FIG. 8a is a partial cross sectional view of a multi-lumen mixing device inserted in a collapsed vertebrae.
Figure 8B:
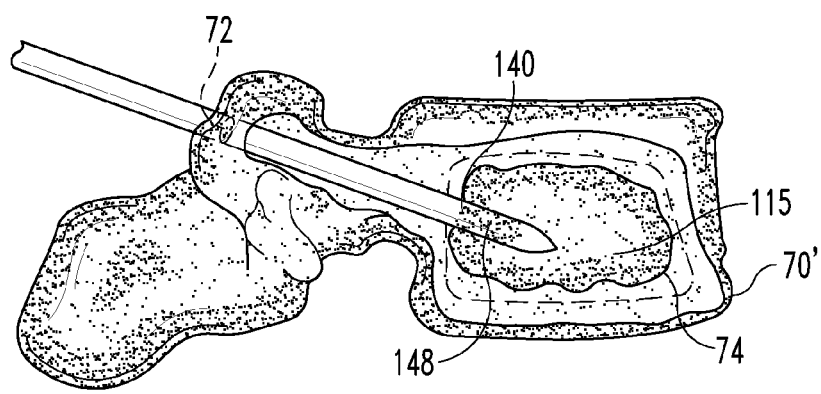
FIG. 8b illustrates the collapsed vertebrae of FIG. 8a repaired with a bone cement injected from the multi-lumen mixing device.

Referring now to FIGS. 8a and 8b, an embodiment of multi-lumen mixing device 130 is illustrated as constructed and arranged as a system for stabilizing a collapsed vertebrae by introducing a bone cement mixture (in the form of combined reagents 115) into the collapsed vertebrae. FIG. 8a illustrates collapsed vertebrae 70 with a compression fracture. Vertebrae 70 may be, for example, in the thoracic or lower spine of the patient. The compression fracture of vertebrae 70 collapses the bone tissue at the vertebrae body. This condition can be caused by osteoporosis, tumor or trauma to the back.

The illustrated embodiment of multi-lumen mixing device 130 can be utilized for stabilizing collapsed vertebrae 70 by either vertebroplasty or kyphoplasty, both of which are medical procedures for restoring structural integrity to collapsed vertebrae. These procedures stabilize collapsed vertebrae 70 by filling in open spaces within the vertebrae body with bone cement to provide a more continuous and solid form. These procedures may also restore an approximate original shape or height to vertebrae 70. It should be noted that the disclosed device and method applies to both vertebroplasty and kyphoplasty and other procedures for stabilizing and/or repairing damaged bone of patients. While the embodiments discussed herein are specifically describing vertebroplasty, a person of ordinary skill in the art will recognize how these teachings apply to the other related procedures.

These procedures are normally performed using an x-ray medical imaging device such as a fluoroscope to enhance visualization. These procedures can be performed under local anesthesia and/or light sedation. A nick is made in the skin near the spine and element 140 is inserted percutaneously into the open spaces of vertebrae 70 through the left or right pedicle of vertebrae 70 as is known in the art. Tip 144 may be used as a cutting instrument to generate a hole in the skin and access hole 72 into vertebrae 70 or an introducer (not illustrated) can be used to generate access holes so that element 140 can be inserted therethrough.

After insertion, a bone cement mixture in the form of combined reagents 115 can be dispensed from multi-lumen mixing device 130 into vertebrae 70 through ports 146 and 147 to form a solid structure 74 that supports the collapsed vertebrae. The bone cement mixture/combined reagents 115 forms a solid structure 74 by chemically reacting or curing the reagents to become solid. Solid structure 74 may be formed within and/or about the collapsed vertebrae to stabilize vertebrae 70' and may help restore vertebrae spacing and alleviate nerve pinching by supporting collapsed vertebrae 70 at least in a compressive mode. Solid structure 74 can substantially fill the open space of the collapsed vertebrae 70 to provide a more dense and continuous vertebrae 70' which can, in some cases, enhance mobility and alleviate pain in the patient.

In one example, the first reagent of combined reagents 115 includes methylmethacrylate, sodium phosphate, or a mixture thereof and the second reagent of combined reagents 115 includes polymethylmethacrylate, monocalcium phosphate, tricalcium phosphate, calcium carbonate or a mixture thereof. The first reagent may also include a radio pacifier or radiopaque material such as derivatives of tungsten, barium, bismuth, etc.

Referring now to FIGS. 9-10, an alternate embodiment of multi-lumen mixing device 130 is illustrated as multi-lumen mixing device 230 which generally includes cannulated element 240 defining lumen 242 and element 250 defining lumens 252 and 253. The distal portion of multi-lumen mixing device 230 defines reaction chamber 260 which generally includes mixing feature 262, reservoir 249 and ports 246 and 247. In the illustrated embodiment, mixing feature 262 is a spiral mixer as discussed above. Other various embodiments can use other mixing features with other mixer configurations including those disclosed above with regard to mixer 162. Mixing feature 262 can be attached to or integrally formed with element 250 and/or element 240 or alternatively mixing feature 262 can float in reaction chamber 260.

The distal end of multi-lumen mixing device 230 is tip 244, reservoir 249 is defined by the lumen between the distal end of mixing feature 262 and tip 244, ports 246 and 247 provide access from reaction chamber 260 to the area outside of multi-lumen mixing device 230. Ports 255 and 256 provide access between lumen 252 and lumen 242 while ports 257 and 258 provide access between lumen 253 and 242. The distal end of lumens 252 and 253 are blocked by occlusion 254 thereby forcing the reagents passing through lumens 252 and 253 to intermix with the reagent passing through lumen 242.

While not illustrated, the multi-lumen mixing device 230 illustrated in FIGS. 9-10 can be connected to an infusion system containing three separate reagents so that tube 237 connects the first reagent to lumen 252, tube 238 connects the second reagent to lumen 253 while tube 239 connects a third reagent to lumen 242. Any known method, including those discussed above with regard to infusion system 108, can be utilized to infuse the three reagents through multi-lumen mixing device 230 to eject a combined reagent from ports 246 and 247.

Referring now to FIGS. 11 and 12, yet another embodiment of a multi-lumen mixing device is illustrated as multi-lumen mixing device 330 that generally includes cannulated element 340 defining lumens 342 and 343. Lumens 342 and 343 merge at junction 345 into a single lumen defining reaction chamber 360 at the distal portion of multi-lumen mixing device 330. Reaction chamber 360 includes mixing feature 362 and ends at port 346 and tip 344. In the illustrated embodiment, mixing feature 362 is a spiral mixer that floats in reaction chamber 360. In other embodiments, mixing feature 362 may be incorporated with or attached to element 340.

In one embodiment, element 340 may be constructed from a standard side-by-side lumen catheter with one lumen collapsed and welded against the other to form the illustrated structure. In yet other embodiments, element 140 can be molded or formed as the illustrated configuration.

While the disclosure has been illustrated and described in detail in the drawings and foregoing description, the same is to be considered as illustrative and not restrictive in character, it being understood that only the preferred embodiments have been shown and described and that all changes and modifications that come within the spirit of the disclosure are desired to be protected.

We claim:

1. A system for use with a patient, the system comprising:
a first reservoir constructed and arranged to contain a first reagent;
a second reservoir constructed and arranged to contain a second reagent; and
a multi-lumen mixing device comprising:
a needle having a tissue penetrating needle tip, the needle defining a first lumen and including a first coupling between the first reservoir and the first lumen that puts the first lumen in fluid communication with the first reservoir,
a cannula defining a second lumen positioned inside the first lumen in a co-axial orientation and defining a first port in a side of the cannula in fluid communication with both the first and second lumens and wherein the second lumen is occluded distally from the first port,
a second coupling between the second reservoir and the second lumen that puts the second lumen in fluid communication with the second reservoir,
a spiral mixer located inside the second lumen distal from the first port,
a mixing chamber defined by the first lumen, wherein the mixing chamber contains the spiral mixer, wherein the mixing chamber is in fluid communication with both the first and second lumens, and
a second port defined in a side of the needle in fluid communication with the mixing chamber, wherein the first and second lumens and the mixing chamber are constructed and arranged to pass into the patient from outside of the patient, wherein the first and second lumens are constructed and arranged to fluidly isolate the first reagent from the second reagent between the first coupling and the mixing chamber, wherein a distal end of said needle is either closed or has a distal opening with a distal cross-sectional area smaller than an internal cross-sectional area of said needle surrounding a distal end of said spiral mixer; and
wherein the spiral mixer is constructed and arranged to mix the first and second reagents together when the second port is within the patient.

2. The system of claim 1, wherein the first lumen defines a third reservoir between the spiral mixer and the second port.

3. The system of claim 1, wherein the spiral mixer is a generally planar structure that has a twisted pattern along its longitudinal axis.

4. The system of claim 1, wherein the second lumen terminates into the first lumen and wherein the spiral mixer is located distally from where the second lumen terminates into the first lumen.

5. The system of claim 1, wherein the spiral mixer is shaped from a distal portion of the cannula.

6. The system of claim 5, further comprising a hub on the first lumen constructed and arranged to receive the cannula inside the first lumen in a co-axial orientation while permitting rotation of the cannula with respect to the first lumen.

7. The system of claim 1, wherein the tissue penetrating needle tip is selected from a group comprising: a beveled cutting edge tip, a saw-toothed cutting edge tip, a pointed end tip, a trocar tip, and a pencil point tip.

8. A multi-lumen medical device for use with a patient, the multi-lumen medical device comprising:
a needle having a tissue penetrating needle tip, the needle defining a first lumen fluidly coupled to a first side port, wherein the first lumen is constructed and arranged to pass a first reagent and wherein the needle and the first lumen are constructed and arranged to pass into the patient from outside the patient;
a first coupling constructed and arranged to couple the first lumen to a first reservoir of the first reagent;
a cannula defining a second lumen positioned inside the first lumen in a co-axial orientation, wherein the second lumen is constructed and arranged to pass a second reagent, wherein the cannula defines a second side port between the second lumen and the first lumen and wherein the second lumen is occluded distally from the second side port;
a second coupling constructed and arranged to fluidly couple the second lumen to a second reservoir of the second reagent;
a mixing chamber in the needle that is in fluid communication with both the first and second lumen, wherein the first and second lumens are constructed and arranged to fluidly isolate the first reagent from the second reagent between the first coupling and the mixing chamber and wherein the mixing chamber is located in a portion of the needle that is constructed and arranged to pass into the patient from outside the patient;
a mixing element on the cannula positioned in the mixing chamber constructed and arranged to mix the first and second reagent as they flow in the mixing chamber to form a mixture, wherein the mixing element is a generally planar structure twisted along its longitudinal axis; and
wherein the first side port is in fluid communication with the mixing chamber, wherein the first side port is constructed and arranged to inject the mixture into the patient after the mixture has been formed in the mixing chamber and wherein a distal end of the needle is either closed or has a distal opening with a distal cross-sectional area smaller than an internal cross-sectional area of the needle surrounding a distal end of the mixing element.

9. The multi-lumen medical device of claim 8, wherein the mixing element and the cannula are unitarily composed of a single piece.

10. The multi-lumen medical device of claim 8, wherein the second side port is positioned proximally from at least a portion of the mixing element.

11. The multi-lumen medical device of claim 8, wherein the second lumen terminates into the first lumen and wherein the mixing element is located distally from where the second lumen terminates into the first lumen.

12. The multi-lumen medical device of claim 8, wherein the mixing element is shaped from a distal portion of the cannula.

13. The multi-lumen medical device of claim 8, wherein a distal end of the cannula is substantially flattened to a generally planar condition along a longitudinal axis of the cannula and is twisted along the longitudinal axis of the cannula.

14. The multi-lumen medical device of claim 8, wherein the tissue penetrating needle tip is selected from the group comprising: a beveled cutting edge tip, a saw-toothed cutting edge tip, a pointed end tip, a trocar tip, and a pencil point tip.

15. The multi-lumen medical device of claim 8, wherein the needle is constructed of a rigid material such as metal.

16. The multi-lumen medical device of claim 8, further comprising a hub on the needle through which the cannula passes, wherein the hub is adapted to permit rotation of the cannula relative to the needle.

17. A method comprising:
penetrating target tissue in a patient's body by cutting or burrowing inside the patient's body with a tissue penetrating needle tip on a needle;
after the needle has penetrated the target tissue, delivering a first reagent through a first lumen of the needle to a mixing chamber defined by the first lumen such that the needle passes into the patient's body from outside of the patient's body, wherein the mixing chamber is positioned inside the patient's body;
delivering a second reagent to the mixing chamber of the needle through a first port in a second lumen in a cannula positioned inside the first lumen in a co-axial orientation, wherein the second reagent is fluidly isolated from the first reagent when the second reagent is in the second lumen;
after the second reagent passes through the first port and as the first and second reagents flow in a distal direction, mixing the first and second reagents by passing them against a mixing element in the mixing chamber thereby forming a combined reagent, wherein the mixing element and the cannula are unitarily composed of a single piece;
injecting the combined reagent through a second side port in the needle that is in fluid communication with the mixing chamber into the target tissue, wherein a distal end of said needle is either closed or has a distal opening with a distal cross-sectional area smaller than an internal cross-sectional area of said needle surrounding a distal end of said mixing element; and
rotating the mixing element with respect to the mixing chamber.

18. The method of claim 17, wherein the mixing element is a generally planar structure that has a twisted pattern along its longitudinal axis.

19. The method of claim 17, further comprising ablating tissue by inserting the multi-lumen mixing device into the target tissue and injecting the combined reagent through the second port into the target tissue, wherein the combined reagent generates an exothermic chemical reaction sufficient to ablate the target tissue.

20. The method of claim 17, further comprising stabilizing a vertebra by inserting the multi-lumen mixing device into the vertebra and injecting the combined reagent through the second port into the vertebra, wherein the combined reagent is a bone cement.

21. The method of claim 17, wherein the cannula defines the second lumen and the mixing element and wherein the cannula is positioned inside the first lumen in a co-axial orientation through a hub, further comprising rotating the cannula and the mixing element with respect to the first lumen while delivering the first and second reagents to the mixing chamber.

* * * * *